United States Patent
Ghigo et al.

(10) Patent No.: US 10,155,965 B2
(45) Date of Patent: Dec. 18, 2018

(54) PRODUCTION OF 1-PROPANOL

(71) Applicants: INSTITUT PASTEUR, Paris (FR); ECOLE SUPERIEURE DE PHYSIQUE ET DE CHIMIE INDUSTRIELLES DE LA VILLE DE PARIS (ESPCI), Paris (FR)

(72) Inventors: Jean-Marc Ghigo, Fontenay-aux-roses (FR); Sabina Chalabaev, Paris (FR); Sylvie Letoffe, Courbevoie (FR); Jose Dugay, Palaiseau (FR)

(73) Assignees: INSTITUT PASTEUR, Paris (FR); ECOLE SUPERIEURE DE PHYSIQUE ET DE CHIMIE INDUSTRIELLES DE LA VILLE DE PARIS (ESPCI), Paris (FR)

(*) Notice: Subject to any disclaimer, the term of this patent is extended or adjusted under 35 U.S.C. 154(b) by 6 days.

(21) Appl. No.: 15/312,147

(22) PCT Filed: Jun. 16, 2015

(86) PCT No.: PCT/IB2015/054548
§ 371 (c)(1),
(2) Date: Nov. 17, 2016

(87) PCT Pub. No.: WO2015/193811
PCT Pub. Date: Dec. 23, 2015

(65) Prior Publication Data
US 2017/0073706 A1  Mar. 16, 2017

Related U.S. Application Data

(60) Provisional application No. 62/012,673, filed on Jun. 16, 2014.

(51) Int. Cl.
| | |
|---|---|
| *C12N 9/88* | (2006.01) |
| *C12P 7/04* | (2006.01) |
| *C12N 9/04* | (2006.01) |
| *C12N 9/02* | (2006.01) |

(52) U.S. Cl.
CPC .............. *C12P 7/04* (2013.01); *C12N 9/0006* (2013.01); *C12N 9/0008* (2013.01); *C12N 9/88* (2013.01); *C12Y 101/01001* (2013.01); *C12Y 102/0101* (2013.01); *C12Y 403/01019* (2013.01)

(58) Field of Classification Search
CPC ...... C12Y 102/0101; C12Y 101/01001; C12Y 403/01019
See application file for complete search history.

(56) References Cited

U.S. PATENT DOCUMENTS

2013/0164805 A1   6/2013  Lee et al.

FOREIGN PATENT DOCUMENTS

| WO | 2008/000809 A1 | 1/2008 |
|---|---|---|
| WO | 2011/088422 A2 | 7/2011 |
| WO | 2012/083244 A2 | 6/2012 |

OTHER PUBLICATIONS

HeBlinger et al. 1998; Novel keto acid formate-lyase and propionate kinase enzymes are components of an anaerobic pathway in *Escherichia coli* that degrades L-threonine to propionate. Molecular Microbiology. 27(2): 477-492.*
Janssen. 2004; Propanol as an end product of threonine fermentation. Arch. Microbiol. 182: 482-486.*
Reisner et al. 2006; In vitro biofilm formation of commensal and pathogenic *Escherichia coli* strains: Impact of environmental and genetic factors. J. Bacteriol. 188(10): 3572-3581.*
Sezonov et al. 2007; *Escherichia coli* physiology in Luria-Bertani broth. J. Bacteriol. 189(23): 8746-8749.*
Ammar Ehab Mohamed et al: "Metabolic engineering of Propionibacterium freudenreichiifom-propanol production", Applied Microbiology and Biotechnology, Springer, DE, vol. 97, No. 10, Apr. 11, 2013 (Apr. 11, 2013), pp. 4677-4690.
Yong Jun Choi et al: "Metabolic engineering of *Escherichia coli* for the production of 1-propanol", Metabolic Engineering, vol. 14, No. 5, Sep. 1, 2012 (Sep. 1, 2012), pp. 477-486.
Kajan Srirangan et al: "Manipulating the sleeping beauty mutase operon for the production of 1-propanol in engineered *Escherichia coli*", Biotechnology for Biofuels, Biomed Central Ltd, GB, vol. 6, No. 1, Sep. 28, 2013 (Sep. 28, 2013), p. 139.

(Continued)

*Primary Examiner* — Karen Cochrane Carlson
(74) *Attorney, Agent, or Firm* — Arrigo, Lee, Guttman & Mouta-Bellum LLP

(57) ABSTRACT

This invention encompasses methods of making 1-propanol. In some embodiments the methods comprise providing a cultured bacterial biofilm; culturing the bacterial biofilm under conditions suitable for production of 1-propanol; and collecting 1-propanol produced by the biofilm culture. In some embodiments the methods comprise providing a bacterial culture comprising bacteria and culture media, wherein the culture media comprises a concentration of threonine higher than that present in LB; maintaining the bacterial culture under conditions suitable for production of 1-propanol; and collecting 1-propanol produced by the culture. This invention also encompasses bacterial culture systems. In some embodiments the bacterial culture systems comprise a bacterial biofilm comprising bacteria growing on an artificial solid substrate; culture media; 1-propanol in liquid and/or gas form; and a collection device configured to collect 1-propanol produced by the culture. In come embodiments the culture systems comprise bacteria; culture media, wherein the culture media comprises a concentration of threonine higher than that present in LB; 1-propanol in liquid and/or gas form; and a collection device configured to collect 1-propanol produced by the culture.

27 Claims, 12 Drawing Sheets

(56) References Cited

OTHER PUBLICATIONS

Yajun Yan et al: "Engineering metabolic systems for production of advanced fuels", Journal of Industrial Microbiology & Biotechnology; Official Journal of the Society for Industrial Microbiology, Springer, Berlin, DE, vol. 36, No. 4, Feb. 7, 2009 (Feb. 7, 2009), pp. 471-479.

Christophe Beloin, et al., "*Escherichia coli* biofilms," Curr Top Microbiol Immunol. 2008; 322: 249-289.

* cited by examiner

PRODUCTION OF 1-PROPANOL

FIELD OF THE INVENTION

The invention concerns methods of producing 1-propanol using bacteria grown in biofilm or planktonic culture. The invention concerns also bacterial culture and bacterial culture systems for producing 1-propanol.

BACKGROUND OF THE INVENTION

The production of fuel substitutes from renewable resources has gained significant attention because of the rising energy price, environmental concerns and the need to reduce dependence on fossil-derived transportation fuels. Currently, ethanol is the major form of biofuel, with 84 billion liters of bioethanol produced in the world in 2011. While both the production capacity and the demand for bioethanol are increasing rapidly, ethanol properties are incompatible with existing fuel infrastructure. Indeed, ethanol's tendency to absorb water poses distribution problems in currently used pipelines and its low energy density (30% lower than gasoline) requires vehicle retrofitting in the fuel system when using high percentage blends with gasoline (Yan & Liao, 2009).

These problems with ethanol hinder large-scale replacement of gasoline. As an alternative, production of higher chain alcohol biofuels (n-propanol, n-butanol, isobutanol, methyl butanol), fatty acid esters and isoprenoids from renewable sources are of increasing interest because of their high energy densities and their low hygroscopicity, which reduce problems in storage and distribution and allow usage in current engines. However, these biofuel compounds with high fuel-quality are not commonly produced biologically (except, for instance, by some *Clostridium* species) and/or in large enough quantities for fuel applications.

1-Propanol ($CH_3CH_2CH_2OH$; n-propanol, propan-1-ol, propylic alcohol, n-Propyl alcohol, Propyl alcohol, Propylol, Ethylcarbinol, 1-Hydroxypropane, Propionic alcohol, Propionyl alcohol, Propionylol) is an important industrial chemical that has been used as a major component of resins and as a carrier and extraction solvent in the pharmaceutical, paint, cosmetic (lotion, soap, and nail polish) and cellulose ester industries. It also has high biofuel potential in terms of combustion efficiency, storage convenience and transportation with an energy density and a flashpoint higher than methanol and ethanol.

Production and uses of 1-propanol are associated with its transformation into compounds such as propionic acid, iso-propanol, propionaldehyde and trihydroxymethyl ethane, all of which are important chemical commodities. Hundreds of thousands of tons of 1-propanol are produced by a two-step process requiring the catalytic hydroformylation of ethylene to produce propanal and then catalytic hydrogenation of the propanal. Alternatively, 1-propanol can also be produced as a by-product of fermentation of potatoes, but unlike ethanol and butanol, very few "green" biofermentation processes exist for the production of this very important commodity.

To circumvent these production issues, metabolic engineers have used genomic information and molecular biology techniques to construct user-friendly, heterologous (non-native) host organisms such as *Escherichia coli* or *Saccharomyces cerevisiae* to serve as a production platform for the production of fuel-grade compounds beyond the scope of what native organisms can produce. Microbial production of 1-propanol has been demonstrated by *Clostridium* sp. and yeast (Eden et al., 2001; Janssen, 2004), with final titers achieved less than 70 mg/L. Recently, a metabolically engineered *Escherichia coli* strain harboring 2-keto acid decarboxylase and alcohol/aldehyde dehydrogenase capable of producing 1 g/L of 1-propanol via 2-ketobutyrate was developed (Shen & Liao, 2013).

The introduction of a modified *Methanococcus jannaschii* citramalate synthase (encoded by cimA) that can directly convert pyruvate to 2-ketobutyrate, led to the production of up to 3.5 g/L of 1-propanol (Atsumi & Liao, 2008) (Howell et al., 1999). *Thermobifida fusca*, a cellulolytic microorganism, harboring the *Clostridium acetobutylicum* ATCC 824 alcohol/aldehyde dehydrogenase also produced 0.48 g/L of 1-propanol from untreated lignocellulosic biomass as a carbon source via 2-ketobutyrate as a metabolic intermediate (Deng & Fong, 2011).

Recently, a wild-type *E. coli* harboring 1,2-propanediol dehydratase from *Klebsiella oxytoca* was shown to produce 0.25 g/L of 1-propanol following additional engineering of the 1,2-propanediol pathway (Jain & Yan, 2011). Finally, production of 1-propanol through an amino acid biosynthetic pathway using glucose or glycerol as a carbon source was achieved in an *E. coli* strain engineered to establish a novel pathway leading to the formation of 1-propanol under aerobic condition and carrying plasmid-based atoDA, adhEmut, thrABC, ackA and cimA genes was able to produce more than 10 g/L of 1-propanol from glucose or glycerol in aerobic fed-batch fermentation (Shen & Liao, 2013, Choi et al., 2012, Shen & Liao, 2008) (Srirangan et al., 2013).

There is a need in the art for efficient means to produce 1-propanol. This invention provides methods, bacterial cultures, and systems to meet this and other needs.

SUMMARY OF THE INVENTION

The Examples demonstrate that bacterial biofilms produce 1-propanol even though the same constituent bacteria grown in planktonic culture may not produce 1-propanol. The examples also demonstrate that threonine is the biogenic precursor for 1-propanol production and that 1-propanol production pathway relies on expression of the adhE gene and the tdc genes located in the tdcABCDEFG operon. The Examples also demonstrate that bacteria grown in liquid (planktonic) culture may be induced to produce 1-propanol by cultivation under anaerobic condition in presence of threonine (or a precursor of threonine) either naturally present in rich culture medium (e.g.: LB, TSB, TYT, TB) or added to the culture media. The threonine precursor stimulates endogenous threonine biosynthesis in the bacteria (FIG. 12). Therefore, this invention provides methods of making 1-propanol using non genetically modified bacteria grown in a biofilm format and/or using bacteria grown in a planktonic culture in presence of threonine and anaerobic conditions. This invention also provides bacterial cultures and systems useful, for example, to produce 1-propanol. This invention also provides evidence that engineered bacteria expressing the genes involved in the propanol pathway (tdcA-G genes and adhE) could produce 1-propanol in biofilm or planktonic condition even in absence of anaerobiosis These and other aspects of the invention are provided herein.

This invention encompasses methods of making 1-propanol. In some embodiments the methods comprise providing a cultured bacterial biofilm; culturing the bacterial biofilm under conditions suitable for production of 1-propanol; and collecting 1-propanol produced by the biofilm culture. In some embodiments the cultured bacterial biofilm is a cultured enterobacteria (Enterobacteriaceae family) biofilm, preferably a cultured *E. coli* biofilm. In some embodiments the cultured biofilm comprises bacteria genetically engineered to overexpress genes involved in the threonine to propanol pathway, including at least one gene selected from adhE, tdcB, ilvA, tdcE, and pflB, preferably at least adhE and/or tdcB. In some embodiments the cultured biofilm comprises bacteria genetically engineered to reduce expression of at least one gene selected from ptA, tdcD, and ackA, preferably at least tdcD. In some embodiments the cultured biofilm comprises bacteria genetically engineered to overexpress at least one gene selected from adhE, tdcB, ilvA, tdcE, and pflB, preferably at least adhE and/or tdcB; and genetically engineered to reduce expression of at least one gene selected from ptA, tdcD, and ackA, preferably at least tdcD. In some embodiments the conditions suitable for production of 1-propanol comprise culture in media comprising a concentration of threonine higher than that present in Lysogeny Broth (LB). In some embodiments the conditions suitable for production of 1-propanol comprise culture in media comprising at least 0.4% (w/v) threonine. In some embodiments the conditions suitable for production of 1-propanol comprise culture in media comprising a threonine precursor, preferably glycine, more preferably at least 0.1%, 0.2%, 0.3%, 0.4%, 0.5%, 0.6%, 0.7% or 0.8% (w/v) glycine. In some embodiments the conditions suitable for production of 1-propanol comprise culture in a rich medium such as with no limitations LB, TSB, TYT or TB, eventually supplemented with threonine or a precursor thereof, as defined above. In some embodiments the methods further comprise providing the cultured bacterial biofilm by a method comprising seeding bacteria onto an artificial solid substrate under conditions sufficient for the bacteria to form a biofilm.

This invention also encompasses bacterial culture systems. In some embodiments the bacterial culture systems comprise a bacterial biofilm comprising bacteria growing on an artificial solid substrate; culture media; 1-propanol in liquid and/or gas form; and a collection device configured to collect 1-propanol produced by the culture. In some embodiments the composition of the constituent bacteria in the biofilm is known. In some embodiments the cultured bacterial biofilm is a cultured enterobacteria biofilm, preferably a cultured *E. coli* biofilm. In some embodiments the cultured biofilm comprises bacteria genetically engineered to overexpress genes involved in the threonine to-propanol pathway, including at least one gene selected from adhE, tdcB, ilvA, tdcE, and pflB, preferably, at least adhE and/or tdcB. In some embodiments the cultured biofilm comprises bacteria genetically engineered to reduce expression of at least one gene selected from ptA, tdcD, and ackA, preferably at least tdcD. In some embodiments the cultured biofilm comprises bacteria genetically engineered to overexpress at least one gene selected from adhE, tdcB, ilvA, tdcE, and pflB, preferably, at least adhE and/or tdcB; and genetically engineered to reduce expression of at least one gene selected from ptA, tdcD, and ackA, preferably, at least tdcD. In some embodiments the culture media comprises a concentration of threonine higher than that present in LB. In some embodiments the culture media comprises at least 0.4% threonine. In some embodiments, the culture media comprises a threonine precursor, preferably glycine, more preferably at least 0.1%, 0.2%, 0.3%, 0.4%, 0.5%, 0.6%, 0.7% or 0.8% (w/v) glycine. In some embodiments the culture medium is a rich medium such as with no limitations LB, TSB, TYT or TB, eventually supplemented with threonine or a precursor thereof, as defined above. This invention also encompasses additional methods of making 1-propanol. In some embodiments the methods comprise providing a bacterial culture comprising bacteria and culture media, wherein the culture media comprises a concentration of threonine higher than that present in LB; maintaining the bacterial culture under conditions suitable for production of 1-propanol; and collecting 1-propanol produced by the culture. In some embodiments the methods comprise providing a cultured of non biofilm, planktonic culture; culturing the planktonic bacteria under anaerobic conditions suitable for production of 1-propanol; and collecting 1-propanol produced by the culture. In some embodiments the bacteria are enterobacteria, preferably *E. coli*. In some embodiments the bacteria are genetically engineered to overexpress at least one gene selected from adhE, tdcB, ilvA, tdcE, and pflB, preferably, at least adhE and/or tdcB. In some embodiments the bacteria are genetically engineered to reduce expression of at least one gene selected from ptA, tdcD, and ackA, preferably at least tdcD. In some embodiments the bacteria are genetically engineered to overexpress at least one gene selected from adhE, tdcB, ilvA, tdcE, and pflB, preferably, at least adhE and/or tdcB; and the bacteria are genetically engineered to reduce expression of at least one gene selected from ptA, tdcD, and ackA, preferably at least tdcD. In some embodiments the culture media comprises at least 0.4% threonine. In some embodiments, the culture media comprises a threonine precursor, preferably glycine, more preferably at least 0.1%, 0.2%, 0.3%, 0.4%, 0.5%, 0.6%, 0.7% or 0.8% (w/v) glycine. In some embodiments the culture medium is a rich medium such as with no limitations LB, TSB, TYT or TB, eventually supplemented with threonine or a precursor thereof, as defined above. This invention also encompasses bacterial cultures. In some embodiments the bacterial cultures comprise bacteria; culture media, wherein the culture media comprises a concentration of threonine higher than that present in LB; and 1-propanol in liquid and/or gas form. In some embodiments the culture comprises bacteria grown in a biofilm. In some embodiments the culture comprises planktonic bacteria. In some embodiments the bacteria are enterobacteria, preferably *E. coli*. In some embodiments the bacteria are genetically engineered to overexpress at least one gene selected from adhE, tdcB, ilvA, tdcE, and pflB, preferably, at least adhE and/or tdcB. In some embodiments the bacteria are genetically engineered to reduce expression of at least one gene selected from ptA, tdcD, and ackA, preferably at least tdcD. In some embodiments the bacteria are genetically engineered to overexpress at least one gene selected from adhE, tdcB, ilvA, tdcE, and pflB, preferably, at least adhE and/or tdcB; and the bacteria are genetically engineered to reduce expression of at least one gene selected from ptA, tdcD, and ackA, preferably at least tdcD. In some embodiments the culture media comprises at least 0.4% threonine. In some embodiments, the culture media comprises a threonine precursor, preferably glycine, more preferably at least 0.1%, 0.2%, 0.3%, 0.4%, 0.5%, 0.6%, 0.7% or 0.8% (w/v) glycine. In some embodiments the culture medium is a rich medium such as with no limitations LB, TSB, TYT or TB, eventually supplemented with threonine or a precursor thereof, as defined above.

This invention also encompasses additional bacterial culture systems. In some embodiments the culture systems comprise bacteria; culture media, wherein the culture media comprises a concentration of threonine higher than that present in LB; 1-propanol in liquid and/or gas form; and a collection device configured to collect 1-propanol produced by the culture. In some embodiments the culture comprises bacteria grown in a biofilm. In some embodiments the culture comprises planktonic bacteria. In some embodiments the bacteria are enterobacteria, preferably *E. coli*. In some embodiments the bacteria are genetically engineered to overexpress at least one gene selected from adhE, tdcB, ilvA, tdcE, and pflB. In some embodiments the bacteria are genetically engineered to reduce expression of at least one gene selected from ptA, tdcD, and ackA. In some embodiments the bacteria are genetically engineered to overexpress at least one gene selected from adhE, tdcB, ilvA, tdcE, and pflB; and the bacteria are genetically engineered to reduce expression of at least one gene selected from ptA, tdcD, and ackA. In some embodiments the culture media comprises at least 0.4% threonine.

DETAILED DESCRIPTION OF THE INVENTION

A. Introduction

Figure 1:
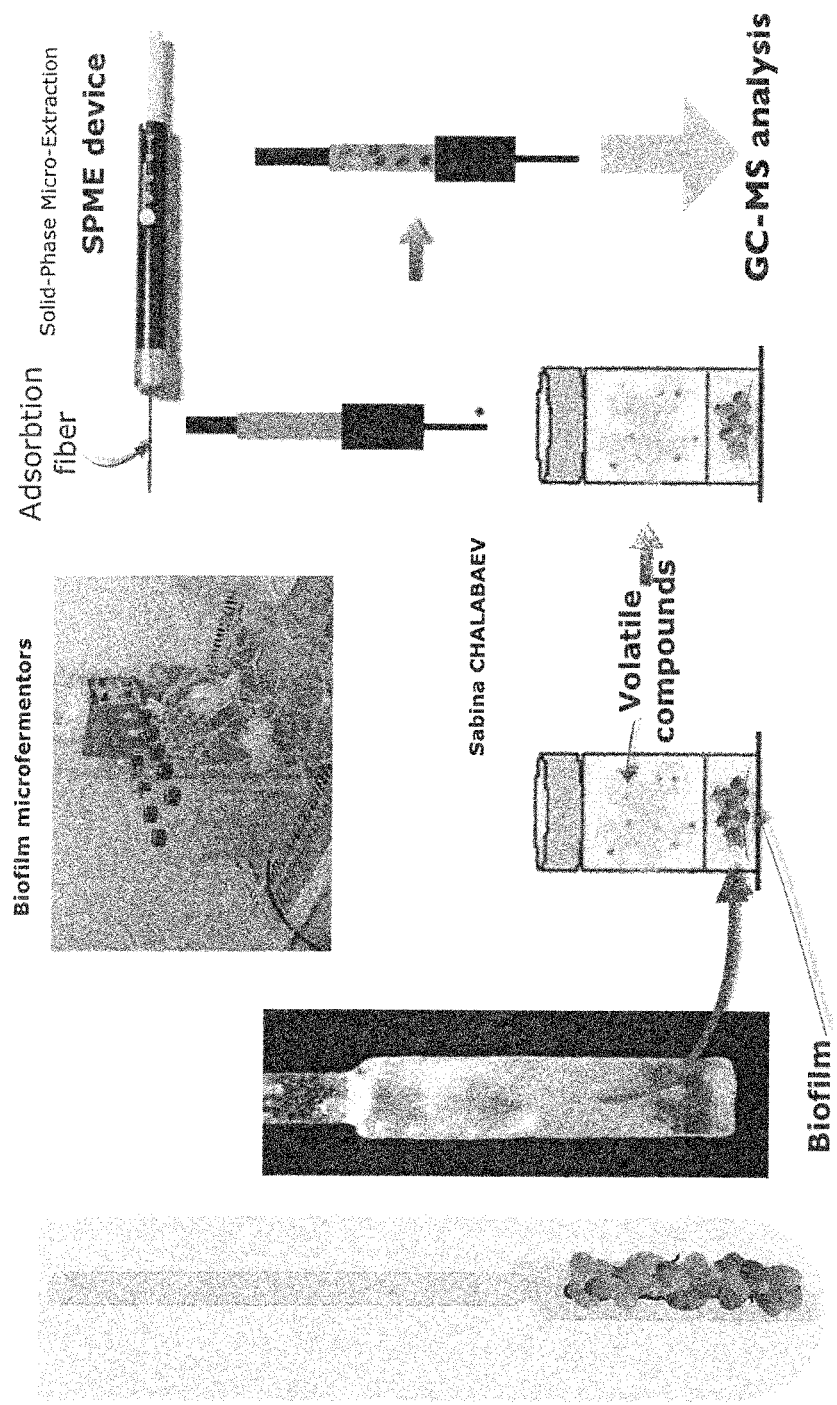
FIG. 1 shows the process that was used to produce biofilm and analyze volatile compounds emitted by bacterial biofilm communities.

The biofilm lifestyle triggers extensive modifications in gene expression that are proposed to correspond to biofilm-specific physiological changes (Ghigo, 2003). The study of biofilm physiological signature suggests profound metabolic rewiring taking place within bacterial biofilm communities compared to non-biofilm bacteria (Beloin et al., 2004, Ghigo, 2003). This leads to the production of various molecules and secondary metabolites (Valle et al., 2008, Rendueles et al., 2011, Rendueles et al., 2013; Rendueles et al., 2014). However, production of 1-propanol by bacterial biofilms has not been previously reported.

B. Definitions

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all UniProt/SwissProt records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3d ed., Cold Spring Harbor Laboratory Press, Cold Spring Harbor, N.Y. (2001); Ausubel et al., Current Protocols in Molecular Biology, Greene Publishing Associates (1992, and Supplements to 2002); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976).

This disclosure refers to sequence database entries (e.g., UniProt/SwissProt records) for certain protein and gene sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present proteins, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

"1-Propanol" is a primary alcohol with the formula $CH_3CH_2CH_2OH$ and is also known by the names n-propanol, propan-1-ol, propylic alcohol, n-Propyl alcohol, Propyl alcohol, Propylol, Ethylcarbinol, 1-Hydroxypropane, Propionic alcohol, Propionyl alcohol, and Propionylol.

As used herein, "recombinant" may refer to a biomolecule, e.g., a gene or protein, or to an organism. The term "recombinant" may be used in reference to cloned DNA isolates, chemically synthesized polynucleotides, or polynucleotides that are biologically synthesized by heterologous systems, as well as proteins or polypeptides and/or RNAs encoded by such nucleic acids. A "recombinant" nucleic acid is a nucleic acid linked to a nucleotide or polynucleotide to which it is not linked in nature. A "recombinant" protein or polypeptide may be (1) a protein or polypeptide linked to an amino acid or polypeptide to which it is not linked in nature; and/or (2) a protein or polypeptide made by transcription and/or translation of a recombinant nucleic acid. Thus, a protein synthesized by a bacteria is recombinant, for example, if it is synthesized from an mRNA synthesized from a recombinant nucleic acid present in the cell. A "recombinant" organism is an organism comprising a "recombinant" biomolecule. For example, a "recombinant" strain of *E. coli* is a strain of *E. coli* that comprises a "recombinant" nucleic acid.

As used herein, an endogenous nucleic acid sequence in the genome of an organism (or the encoded protein product of that sequence) is deemed "recombinant" herein if a heterologous sequence is placed adjacent to the endogenous nucleic acid sequence. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, an "expression control sequence" refers to polynucleotide sequences which affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, a "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors"). The integrating cosmid vector pYUB412 is an example of a "vector".

The term "recombinant host cell" (or simply "recombinant cell" or "host cell"), as used herein, is intended to refer to a cell into which a recombinant nucleic acid such as a recombinant vector has been introduced. In some instances the word "cell" is replaced by a name specifying a type of cell. For example, a "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

The term "genetically engineered", as used herein, is intended to refer to a bacterial cell that comprises a recombinant nucleic acid. The recombinant nucleic acid may be a recombinant form of an endogenous nucleic acid. The recombinant nucleic acid may be a recombinant vector. Methods of making genetically engineered bacteria are well known in the art.

As used herein, the phrase "bacteria genetically engineered to overexpress at least one gene" means that the bacteria are genetically engineered to express a gene at a higher level than the bacteria would normally express under a particular set of conditions. In some embodiments the gene is not normally present in the genome of the bacteria. In some embodiments the bacteria are genetically engineered to contain additional copies of the gene. In some embodiments the gene is a gene selected from alcohol/acetaldehyde dehydrogenase (adhE), catabolic threonine dehydratase tdcB (tdcB), threanine deaminase (ilvA), 2-ketobutyrate formate-lyase (tdcE) gene, and pyruvate formate lyase I (pflB).

As used herein, the phrase "bacteria genetically engineered to reduce expression of at least one gene" means that the bacteria are genetically engineered to express a gene at a lower level than the bacteria would normally express under a particular set of conditions, or to not express a gene that the bacteria would normally express under a particular set of conditions. In some embodiments the gene is present in the genome of the bacteria is mutated through genetic engineering. In some embodiments the gene is selected from phosphate acetyltransferase (ptA), propionate kinase (tdcD), and acetate kinase (ackA).

As used herein, "biofilm" means an aggregated community of at least one type of bacteria and optionally other microbes, that adhere to each other and to other organic and/or inorganic substrates. A unique feature of a biofilm that distinguishes it from its separate "non-aggregated" components is the self-production and secretion of extracellular polymeric substances (EPS) (e.g., carbohydrates, proteins, nucleic acids and other biopolymers) that form a matrix in which the cellular aggregates are embedded.

C. Methods of Making 1-Propanol Using Biofilms

This invention encompasses methods of making 1-propanol. In some embodiments the methods comprise providing a cultured bacterial biofilm; culturing the bacterial biofilm under conditions suitable for production of 1-propanol; and collecting 1-propanol produced by the biofilm culture. Methods for culturing bacteria in biofilm are known in the art (see for example Ghigo, 2001).

In some embodiments the bacterial biofilm comprises a single type of bacteria. In some embodiments the bacterial biofilm comprises a plurality of different types of bacteria. In some embodiments all of the types of bacteria in the biofilm produce 1-propanol. In some embodiments the biofilm comprises at least one type of bacteria that does not produce 1-propanol. In some embodiments the cultured bacterial biofilm comprises enterobacteria, preferably *E. coli*. In some embodiments the cultured bacterial biofilm consists of *E. coli*.

In some embodiments the conditions suitable for production of 1-propanol in biofilm are microaerobic (mid aerobic; typically 2 to 10% $O_2$) conditions or anaerobic conditions. In some embodiments the conditions suitable for production of 1-propanol comprise culture in media comprising a concentration of threonine higher than that present in LB. In some embodiments the conditions suitable for production of 1-propanol comprise culture in media comprising at least 0.2% threonine, at least 0.4% threonine, at least 0.6% threonine, at least 0.8% threonine, at least 1.0% threonine, at least 1.2% threonine, at least 1.4% threonine, at least 1.6% threonine, at least 1.8% threonine, at least 2.0% threonine, at least 2.5% threonine, at least 3% threonine, at least 3.5% threonine, at least 4.0% threonine, at least 4.5% threonine, or at least 5.0% threonine. In some embodiments, the conditions suitable for production of 1-propanol comprise culture in media comprising a threonine precursor, preferably glycine, more preferably at least 0.1%, 0.2%, 0.3%, 0.4%, 0.5%, 0.6%, 0.7% or 0.8% (w/v) glycine. In some embodiments the conditions suitable for production of 1-propanol comprise culture in a rich medium such as with no limitations LB, TSB, TYT or TB, eventually supplemented with threonine or a precursor thereof, as defined above. In some embodiments the conditions suitable for production of 1-propanol comprise flow conditions. In some embodiments the conditions suitable for production of 1-propanol comprise culturing the bacterial biofilm for a period of at least 12 hours, at least 24 hours, at least 48 hours, at least 72 hours, or at least 96 hours.

In some embodiments the cultured biofilm comprises bacteria genetically engineered to overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB.

In some embodiments the cultured biofilm comprises bacteria genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

In some embodiments the cultured biofilm comprises bacteria genetically engineered to (1) overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB; and (2) genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

D. Methods of Making 1-Propanol Using Bacterial Cultures Comprising Threonine

This invention also encompasses methods of making 1-propanol comprising culturing bacteria in the presence of threonine or a precursor thereof. In some embodiments the methods comprise providing a bacterial culture comprising bacteria and culture media, wherein the culture media comprises a concentration of threonine higher than that present in LB; maintaining the bacterial culture under conditions suitable for production of 1-propanol; and collecting 1-propanol produced by the culture.

In some embodiments the bacterial culture comprises a single type of bacteria. In some embodiments the bacterial culture comprises a plurality of different types of bacteria. In some embodiments all of the types of bacteria in the bacterial culture produce 1-propanol. In some embodiments the bacterial culture comprises at least one type of bacteria that does not produce 1-propanol. In some embodiments the bacterial culture comprises enterobacteria, preferably *E. coli*. In some embodiments the bacterial culture consists of *E. coli*.

In some embodiments the culture comprises a bacterial biofilm. In some embodiments the conditions suitable for biofilm production of 1-propanol are anaerobic conditions or microaerobic (mid aerobic) conditions.

In some embodiments the culture comprises planktonic bacteria. In some embodiments the conditions suitable for planktonic production of 1-propanol are aerobic conditions. In some embodiments the conditions suitable for planktonic production of 1-propanol are anaerobic conditions or microaerobic (mid aerobic) conditions. In some embodiments the conditions suitable for production of 1-propanol comprise culture in media comprising a concentration of threonine higher than that present in LB. In some embodiments the conditions suitable for production of 1-propanol comprise culture in media comprising at least 0.2% threonine, at least 0.4% threonine, at least 0.6% threonine, at least 0.8% threonine, at least 1.0% threonine, at least 1.2% threonine, at least 1.4% threonine, at least 1.6% threonine, at least 1.8% threonine, at least 2.0% threonine, at least 2.5% threonine, at least 3% threonine, at least 3.5% threonine, at least 4.0% threonine, at least 4.5% threonine, or at least 5.0% threonine. In some embodiments, the conditions suitable for production of 1-propanol comprise culture in media comprising a threonine precursor, preferably glycine, more preferably at least 0.1%, 0.2%, 0.3%, 0.4%, 0.5%, 0.6%, 0.7% or 0.8% (w/v) glycine. In some embodiments the conditions suitable for production of 1-propanol comprise culture in a rich medium such as with no limitations LB, TSB, TYT or TB, eventually supplemented with threonine or a precursor thereof, as defined above.

In some embodiments the bacterial culture comprises bacteria genetically engineered to overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB.

In some embodiments the bacterial culture comprises bacteria genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

In some embodiments the bacterial culture comprises bacteria genetically engineered to (1) overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB; and (2) genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

E. Bacterial Culture Systems Comprising a Biofilm

This invention also encompasses bacterial culture systems. In some embodiments the bacterial culture systems comprise a bacterial biofilm comprising bacteria growing on an artificial solid substrate; culture media; 1-propanol in liquid and/or gas form; and a collection device configured to collect 1-propanol produced by the culture.

In some embodiments the composition of the constituent bacteria in the biofilm of the bacterial culture systems is known. In some embodiments the bacterial biofilm of the bacterial culture systems comprises a single type of bacteria. In some embodiments the bacterial biofilm of the bacterial culture systems comprises a plurality of different types of bacteria. In some embodiments all of the types of bacteria in the biofilm of the bacterial culture systems produce 1-propanol. In some embodiments the biofilm of the bacterial culture systems comprises at least one type of bacteria that does not produce 1-propanol. In some embodiments the cultured bacterial biofilm of the bacterial culture systems comprises enterobacteria, preferably *E. coli*. In some embodiments the cultured bacterial biofilm of the bacterial culture systems consists of *E. coli*.

In some embodiments the bacterial culture systems provide for culture the bacterial biofilm under anaerobic conditions or microaerobic (mid aerobic) conditions. In some embodiments of the bacterial culture systems the culture media comprises a concentration of threonine higher than that present in LB. In some embodiments of the bacterial culture systems the culture media comprises a concentration of threonine of at least 0.2% threonine, at least 0.4% threonine, at least 0.6% threonine, at least 0.8% threonine, at least 1.0% threonine, at least 1.2% threonine, at least 1.4% threonine, at least 1.6% threonine, at least 1.8% threonine, at least 2.0% threonine, at least 2.5% threonine, at least 3% threonine, at least 3.5% threonine, at least 4.0% threonine, at least 4.5% threonine, or at least 5.0% threonine. In some embodiments of the bacterial culture systems, the culture media comprises a threonine precursor, preferably glycine, more preferably at least 0.1%, 0.2%, 0.3%, 0.4%, 0.5%, 0.6%, 0.7% or 0.8% (w/v) glycine. In some embodiments of the bacterial culture systems, the culture media is a rich medium such as with no limitations LB, TSB, TYT or TB, eventually supplemented with threonine or a precursor thereof, as defined above.

In some embodiments of the bacterial culture systems the culture media is flowed over the biofilm.

In some embodiments of the bacterial culture systems the cultured biofilm comprises bacteria genetically engineered to overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB.

In some embodiments of the bacterial culture systems the cultured biofilm comprises bacteria genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

In some embodiments of the bacterial culture systems the cultured biofilm comprises bacteria genetically engineered to (1) overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB; and (2) genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

F. Bacterial Culture Systems Comprising Threonine

This invention also encompasses additional bacterial culture systems. In some embodiments the culture systems comprise bacteria; culture media, wherein the culture media comprises a concentration of threonine higher than that present in LB; 1-propanol in liquid and/or gas form; and a collection device configured to collect 1-propanol produced by the culture.

In some embodiments the culture systems comprise bacteria grown in a biofilm. In some embodiments the culture systems provide for culture of the bacteria in anaerobic conditions or microaerobic (mid aerobic) conditions.

In some embodiments the culture comprises planktonic bacteria. In some embodiments the culture systems provide for culture of the bacteria in aerobic conditions. In some embodiments the culture systems provide for culture of the bacteria in anaerobic conditions or microacrobic (mid aerobic) conditions. In some embodiments the composition of the constituent bacteria in the biofilm of the bacterial culture systems is known. In some embodiments the bacterial biofilm of the bacterial culture systems comprises a single type of bacteria. In some embodiments the bacterial biofilm of the bacterial culture systems comprises a plurality of different types of bacteria. In some embodiments all of the types of bacteria in the biofilm of the bacterial culture systems produce 1-propanol. In some embodiments the biofilm of the bacterial culture systems comprises at least one type of bacteria that does not produce 1-propanol. In some embodiments the cultured bacterial biofilm of the bacterial culture systems comprises enterobacteria, preferably *E. coli*. In some embodiments the cultured bacterial biofilm of the bacterial culture systems consists of *E. coli*.

In some embodiments the bacterial culture systems provide for culture of the bacterial biofilm under anaerobic conditions or mid aerobic conditions. In some embodiments the bacterial culture systems provide for culture of the planktonic bacteria under aerobic conditions. In some embodiments the bacterial culture systems provide for culture of the planktonic bacteria in anaerobic conditions or microaerobic (mid aerobic) conditions. In some embodiments of the bacterial culture systems the culture media comprises a concentration of threonine higher than that present in LB. In some embodiments of the bacterial culture systems the culture media comprises a concentration of threonine of at least 0.2% threonine, at least 0.4% threonine, at least 0.6% threonine, at least 0.8% threonine, at least 1.0% threonine, at least 1.2% threonine, at least 1.4% threonine, at least 1.6% threonine, at least 1.8% threonine, at least 2.0% threonine, at least 2.5% threonine, at least 3% threonine, at least 3.5% threonine, at least 4.0% threonine, at least 4.5% threonine, or at least 5.0% threonine. In some embodiments of the bacterial culture systems, the culture media comprises a threonine precursor, preferably glycine, more preferably at least 0.1%, 0.2%, 0.3%, 0.4%, 0.5%, 0.6%, 0.7% or 0.8% (w/v) glycine. In some embodiments of the bacterial culture systems, the culture media is a rich medium such as with no limitations LB, TSB, TYT or TB, eventually supplemented with threonine or a precursor thereof, as defined above.

In some embodiments of the bacterial culture systems the culture media is flowed over the biofilm.

In some embodiments of the bacterial culture systems the cultured biofilm comprises bacteria genetically engineered to overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB.

In some embodiments of the bacterial culture systems the cultured biofilm comprises bacteria genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

In some embodiments of the bacterial culture systems the cultured biofilm comprises bacteria genetically engineered to (1) overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, idcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB; and (2) genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

G. Bacterial Cultures

This invention also encompasses bacterial cultures. In some embodiments the bacterial cultures comprise bacteria; culture media, wherein the culture media comprises a concentration of threonine higher than that present in LB; and 1-propanol in liquid and/or gas form.

In some embodiments the culture comprises bacteria grown in a biofilm. In some embodiments the culture comprises planktonic bacteria.

In some embodiments the composition of the constituent bacteria in cultures is known. In some embodiments the cultures comprise a single type of bacteria. In some embodiments the cultures comprise a plurality of different types of bacteria. In some embodiments all of the types of bacteria in the cultures produce 1-propanol. In some embodiments the cultures comprise at least one type of bacteria that does not produce 1-propanol. In some embodiments the cultures comprise enterobacteria, preferably *E. coli*. In some embodiments the cultures consist of *E. coli*.

In some embodiments the culture is an anaerobic, or mid aerobic culture. In some embodiments of the cultures the culture media comprises a concentration of threonine higher than that present in LB. In some embodiments of the cultures the culture media comprises a concentration of threonine of at least 0.2% threonine, at least 0.4% threonine, at least 0.6% threonine, at least 0.8% threonine, at least 1.0% threonine, at least 1.2% threonine, at least 1.4% threonine, at least 1.6% threonine, at least 1.8% threonine, at least 2.0% threonine, at least 2.5% threonine, at least 3% threonine, at least 3.5% threonine, at least 4.0% threonine, at least 4.5% threonine, or at least 5.0% threonine. In some embodiments of the cultures, the culture media comprises a threonine precursor, preferably glycine, more preferably at least 0.1%, 0.2%, 0.3%, 0.4%, 0.5%, 0.6%, 0.7% or 0.8% (w/v) glycine. In some embodiments of the culture, the culture media is a rich medium such as with no limitations LB, TSB, TYT or TB, eventually supplemented with threonine or a precursor thereof, as defined above.

In some embodiments of the bacterial culture the culture media is flowed over the biofilm.

In some embodiments of the cultures the cultured biofilm comprises bacteria genetically engineered to overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB.

In some embodiments of the cultures the cultured biofilm comprises bacteria genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

In some embodiments of the cultures the cultured biofilm comprises bacteria genetically engineered to (1) overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB; and (2) genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

H. Engineered Bacteria

This invention also encompasses engineered bacteria. In some embodiments the engineered bacteria are provided as a biofilm. In some embodiments the engineered bacteria are provided as a planktonic culture. In some embodiments, the engineered planktonic bacteria are cultured under aerobic conditions.

In some embodiments the engineered bacteria is enterobacteria, preferably *E. coli*.

In some embodiments the engineered bacteria are genetically engineered to overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB.

In some embodiments the engineered bacteria are genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

In some embodiments the engineered bacteria are genetically engineered to (1) overexpress at least one gene selected from adhE, tdcB, ilvA, tdcE, and pflB, at least two genes selected from adhE, tdcB, ilvA, tdcE, and pflB, at least three genes selected from adhE, tdcB, ilvA, tdcE, and pflB, at least four genes selected from adhE, tdcB, ilvA, tdcE, and pflB, said gene(s) preferably including adhE and/or tdcB; or all of the genes adhE, tdcB, ilvA, tdcE, and pflB; and (2) genetically engineered to reduce expression of at least one gene selected from ptA, tdcD, and ackA, at least two genes selected from ptA, tdcD, and ackA, said gene(s) preferably including tdcD; or all of the genes ptA, tdcD, and ackA.

EXAMPLES

Example 1: Detection of 1-Propanol Production from Biofilms

Material and Methods

Biofilm formation in continuous-flow microfermentors was performed as previously described in Ghigo, 2001. Briefly, continuous-flow microfermentors containing a removable glass spatula were used to maximize biofilm development and minimize planktonic growth. Inoculation was performed by dipping the glass spatula for 2 min in a culture adjusted to an optical density at 600 nm ($OD_{600}$) of 1 from overnight bacterial cultures grown in rich medium. The spatula was then reintroduced into the microfermentor, and biofilm culture was performed at 37° C. in rich medium supplemented or not with threonine. Propanol produced in the biofilm microfermentor or produced by the biofilm biomass developing on the spatula's surface was analyzed by Gas chromatography Mass spectrometry (GC-MS).

Results

While investigating the nature and role of volatile compounds produced by bacterial biofilm, we developed an SPME-GC-MS approach to compare the nature of the volatile compounds emitted from biofilm and planktonic cultures (FIG. 1).

Figure 2:
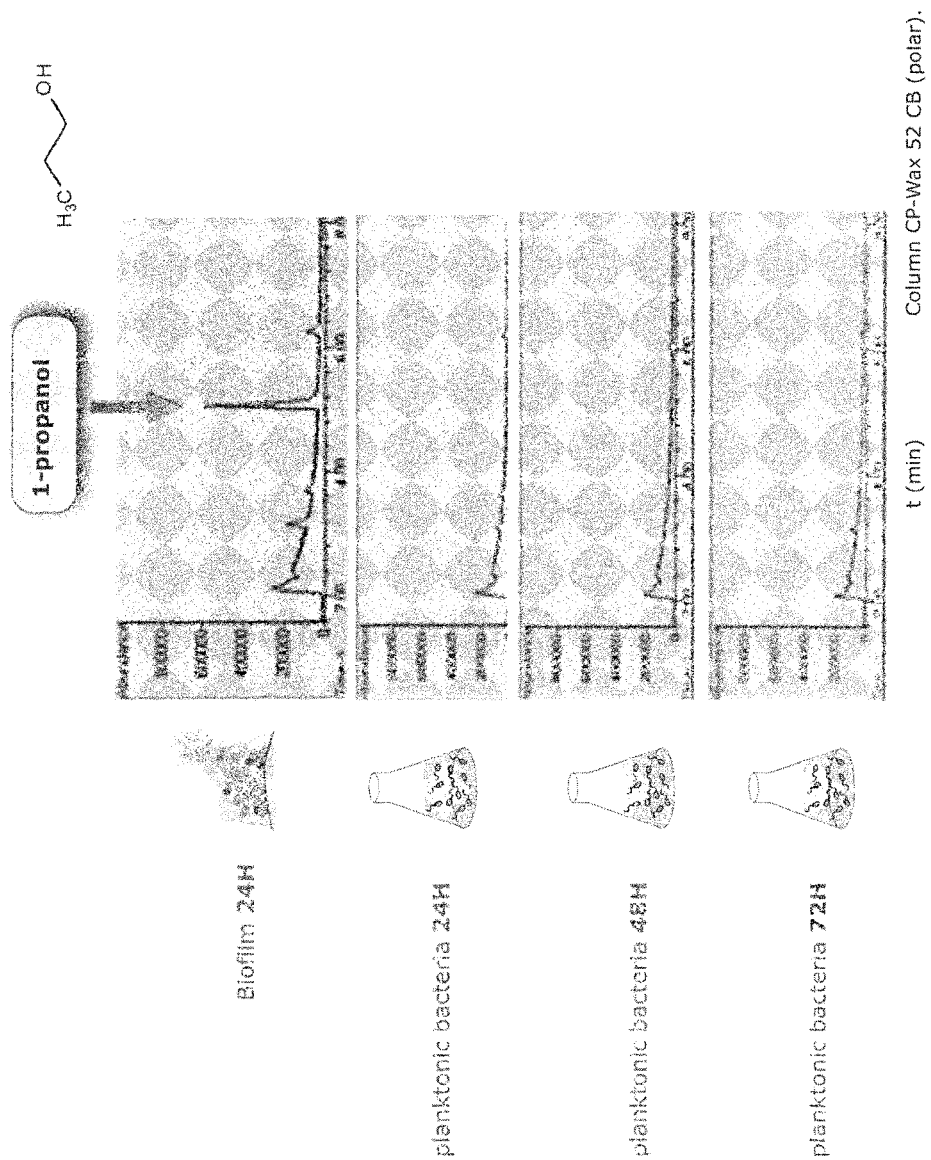
FIG. 2 shows initial results demonstrating biofilm-specific detection of 1-propanol by SPME-GC-MS whereas no 1-propanol is detected in planktonic culture, both types of culture in anaerobic conditions.

We showed that, although no 1-propanol could be detected in the head-space of bacteria cultivated in classical aerobic or anaerobic (planktonic) liquid conditions (exponential phase—5 h; stationary phase—24 h up to 72 h) planktonic bacteria cultured in rich medium (e.g. LB), 1-propanol is emitted by *E. coli* K-12 biofilm communities (FIG. 2).

Figure 3:
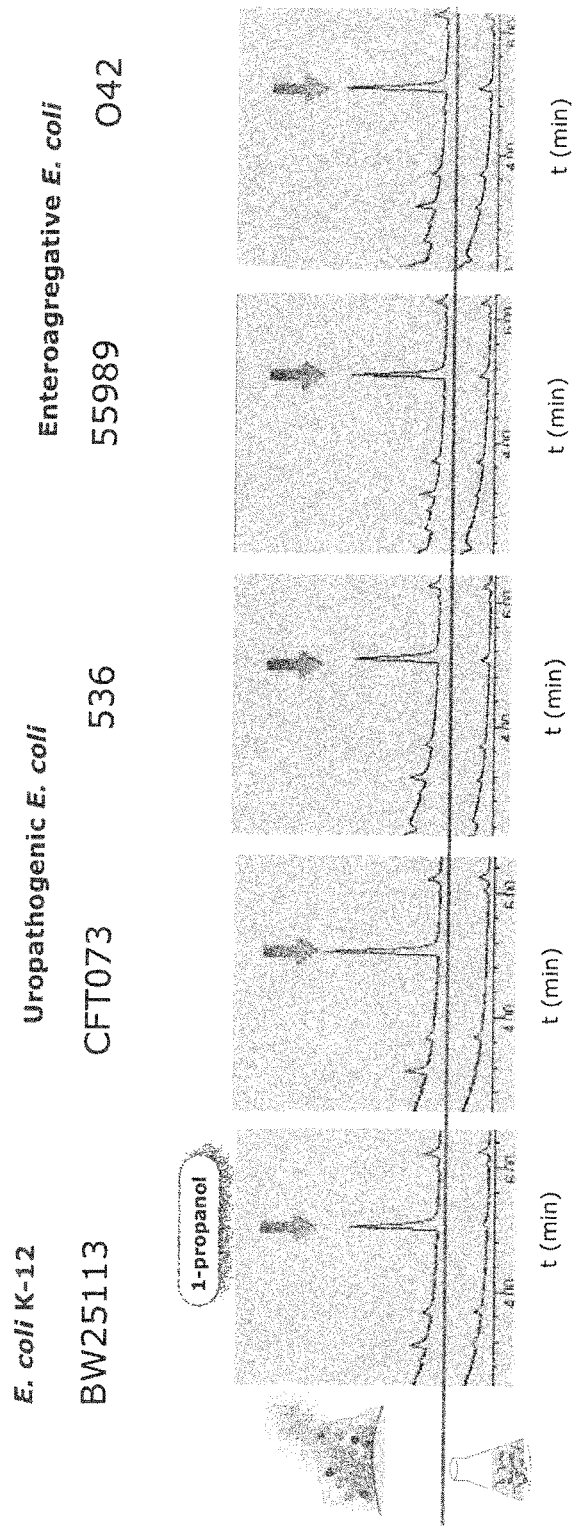
FIG. 3 shows biofilm-specific detection of 1-propanol by SPME-GC-MS in biofilm formed by a variety of commensal and pathogenic *E. coli* strains.

To the best of our knowledge, neither *E. coli* bacteria, nor bacterial biofilm in general were ever reported as natural producer of detectable quantity of 1-propanol. In addition, we showed that 1-propanol is produced by all tested *E. coli* isolates when grown as biofilms in dynamic flow conditions favoring formation of thick mature biofilms (FIG. 3).

Example 2: Role of the *E. coli* Enzyme AdhE (Aldehyde-Alcohol Dehydrogenase)

Figure 4:
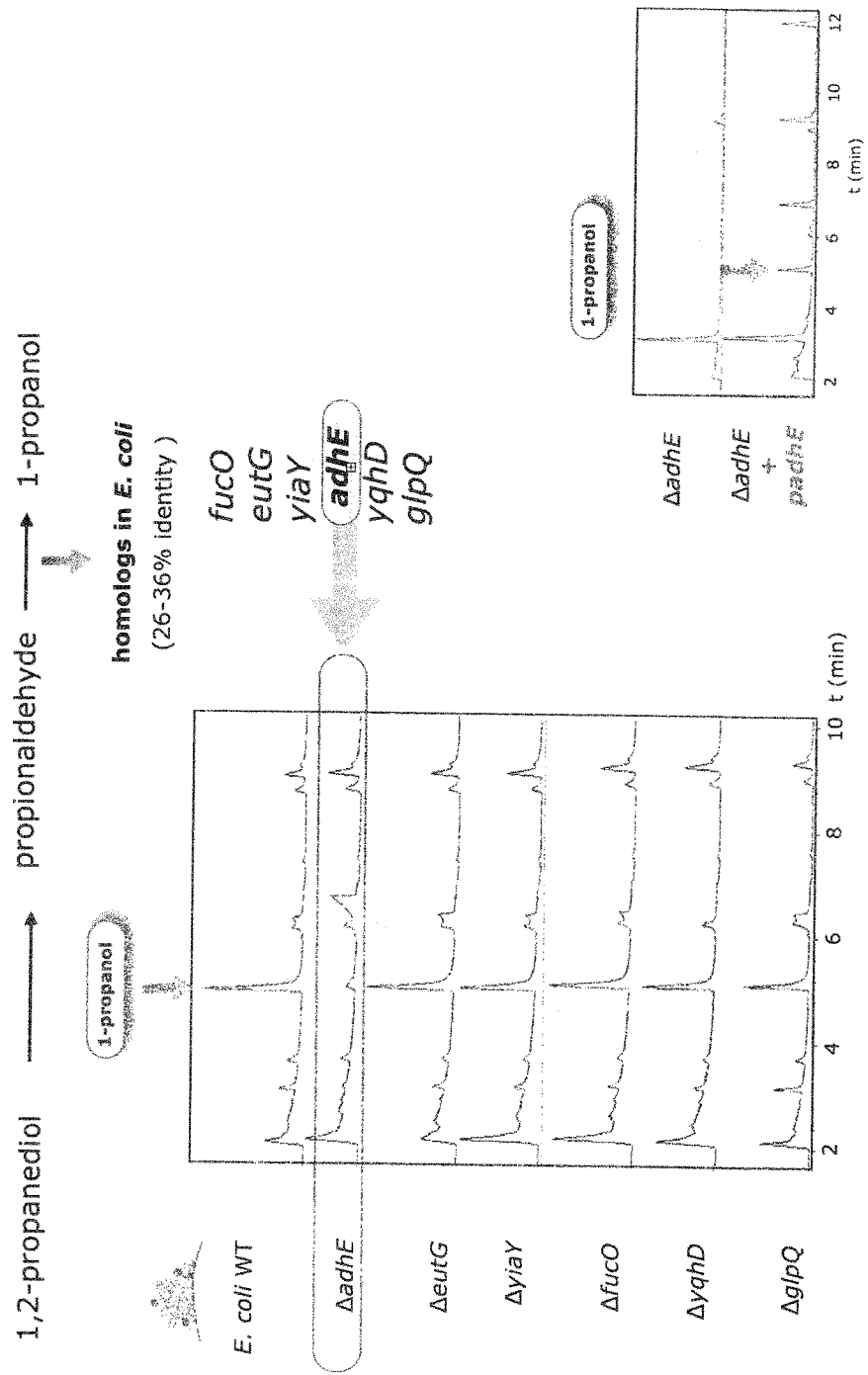
FIG. 4 shows that a mutation in *E. coli* adhE abolishes biofilm-specific 1-propanol production.

To characterize the metabolic pathway used by biofilm bacteria to produce 1-propanol, we tested several *E. coli* mutants for genes displaying homologies with genes involved in 1-propanol production in other organisms. Using this strategy, we demonstrated the role of the aldehyde-alcohol dehydrogenase enzyme AdhE (encoded by the gene adhE (also known as adhC or ana) in biofilm-associated 1-propanol production in *E. coli* (FIG. 4). The adhE-dependent 1-propanol production in biofilm could correspond to several potential metabolic pathway theoretically deduced from pathways known or suspected to exist in other bacteria.

Figure 5:
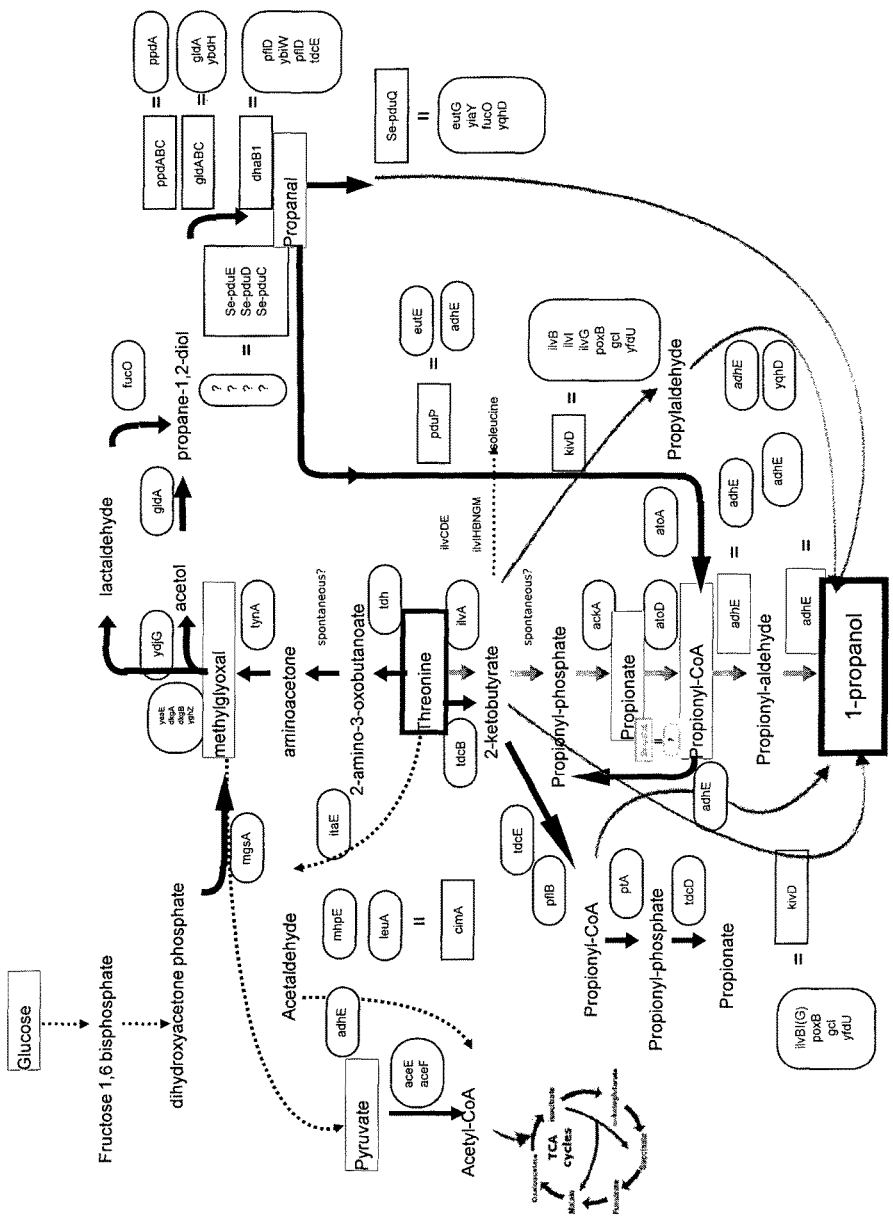
FIG. 5 shows analysis of potential metabolic pathways and screening for genes involved in biofilm-specific propanol production.

Example 3: Identification of Threonine as a Precursor Substrate Increasing 1-Propanol Production To further characterize the metabolic pathway leading to biofilm-associated production of 1-propanol, we tested the effect of potential adhE-dependent 1-propanol precursors. While the threonine concentration in LB has been determined previously (Sezonov et al., 2007) and evaluated to about 0.05% (w/v), we found that addition of Threonine (0.4%) to LB medium increased propanol production (FIG. 5), suggesting that the adhE-dependent pathway leading to 1-propanol used threonine as a precursor. Addition of propanal also led to propanol production.

Figure 6:
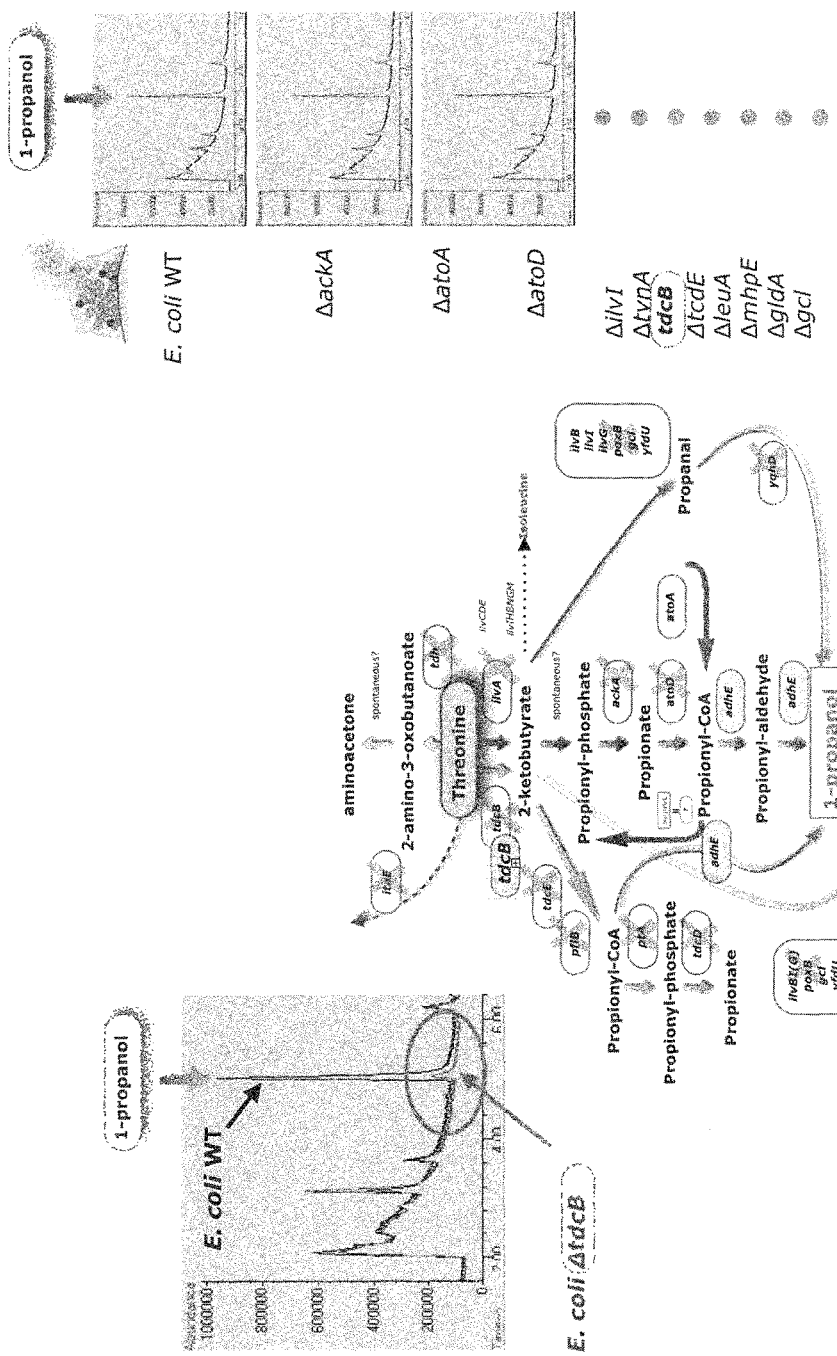
FIG. 6 shows that biofilm propanol production relies on expression of the adhE gene and tdc operon.
Figure 7:
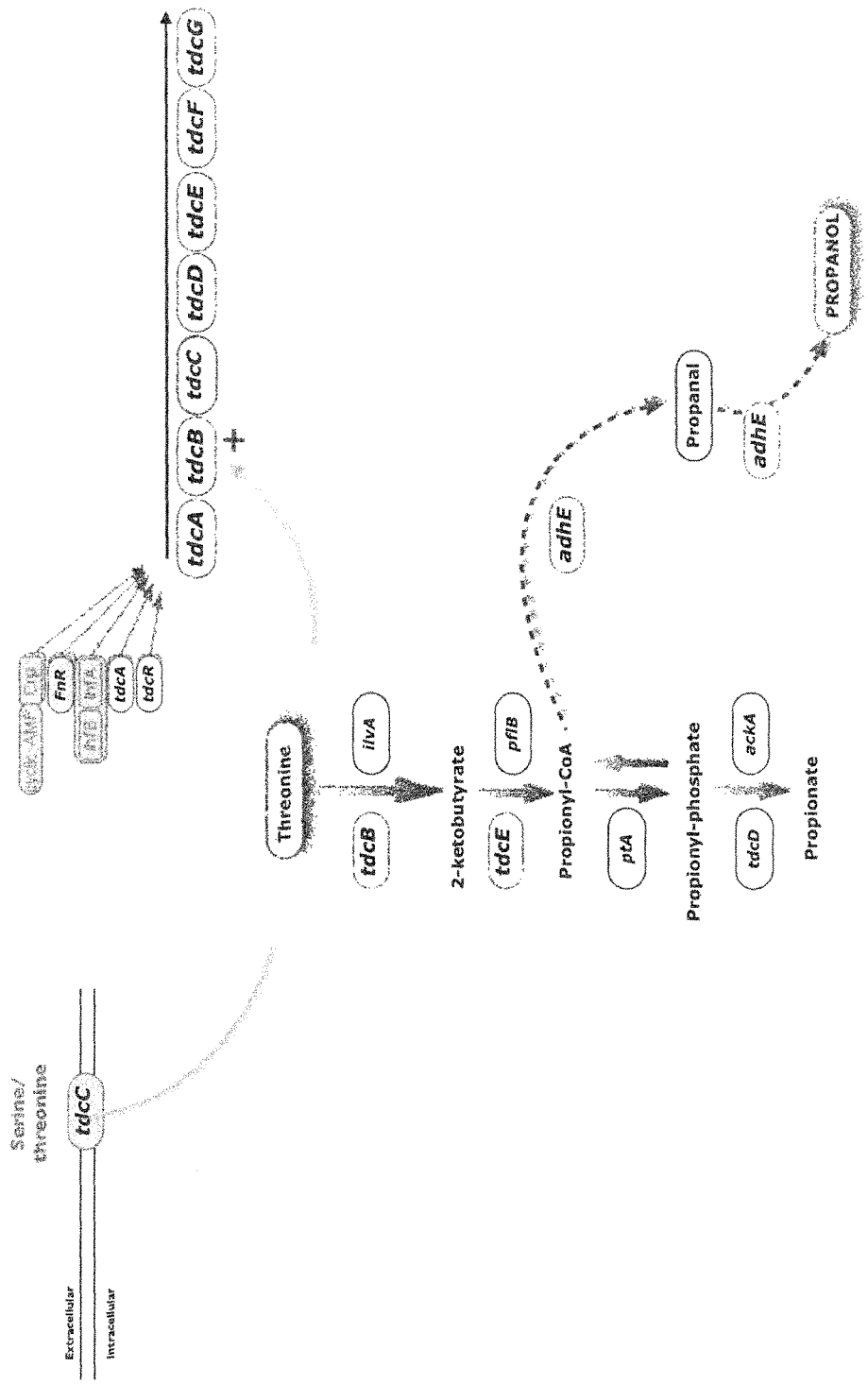
FIG. 7 shows the proposed pathway for 1-propanol production in *E. coli* biofilm.
Figure 8:
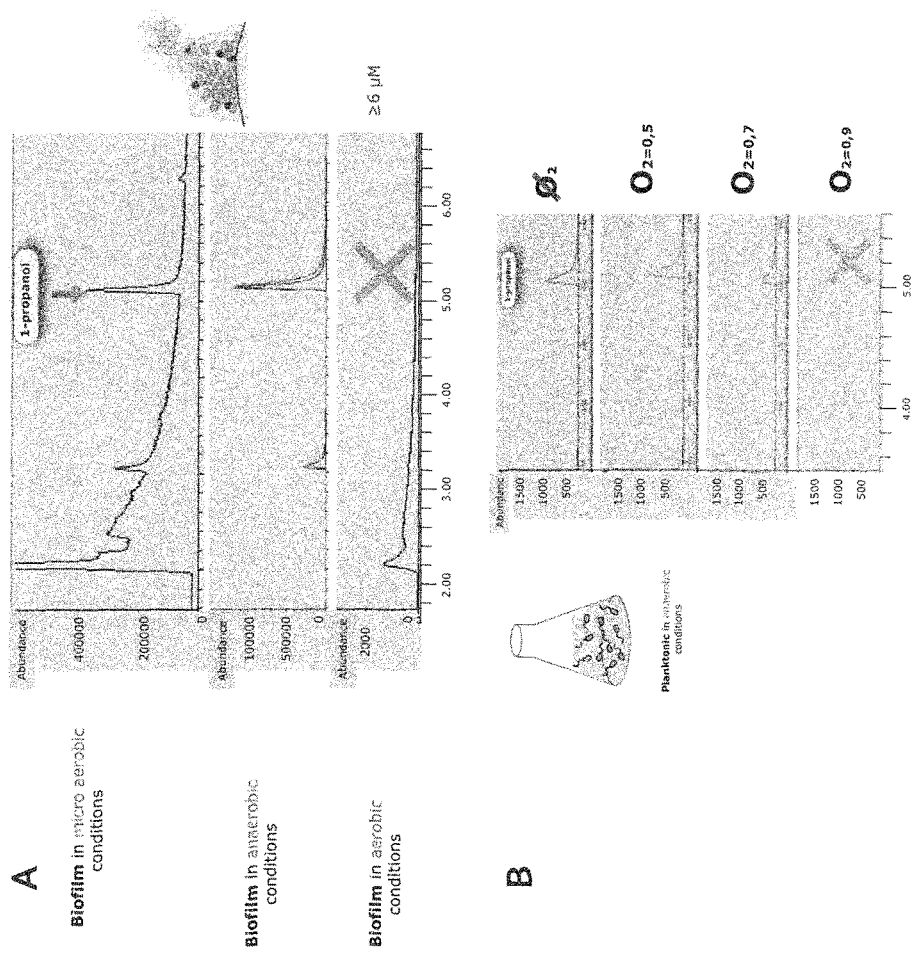
FIG. 8 shows that additional data demonstrating that 1-propanol production by biofilms and by planktonic cultures of bacteria may depend on aerobic or anaerobic conditions. A. As shown the data demonstrate that an *E. coli* biofilm cultured in micro aerobic conditions produces 1-propanol. The data also demonstrate that an *E. coli* biofilm cultured in anaerobic conditions produces 1-propanol. However, an *E. coli* biofilm cultured in aerobic conditions did not produce 1-propanol. B. A planktonic culture of *E. coli* cultured in anaerobic or microaerobic conditions also did produce 1-propanol.

Example 4: Characterization of Biofilm-Associated 1-Propanol Production Pathway in E. coli We tested various mutants in the potential pathways leading from threonine to 1-propanol. This enabled us to identify several mutants impaired or altering 1-propanol yield, leading to the characterization of the metabolic pathway most probably used by *E. coli* to produce 1-propanol during biofilm growth in LB rich medium (FIGS. 6 and 7). The tdcA-G operon is induced both by anaerobic or microaerobic conditions and the presence of Threonine, it encodes for a threonine surface transporters (TdcC) and several enzymes involved in the degradation of threonine. AdheE is induced by anaerobic or microaerobic conditions and possess a broad spectrum coenzyme A-dependent acetaldehyde dehydrogenase et alcohol dehydrogenase activity. Consistently, 1-propanol production by biofilms and by planktonic cultures of bacteria may depend on aerobic or anaerobic conditions (FIGS. 8A and 8B).

Figure 9:
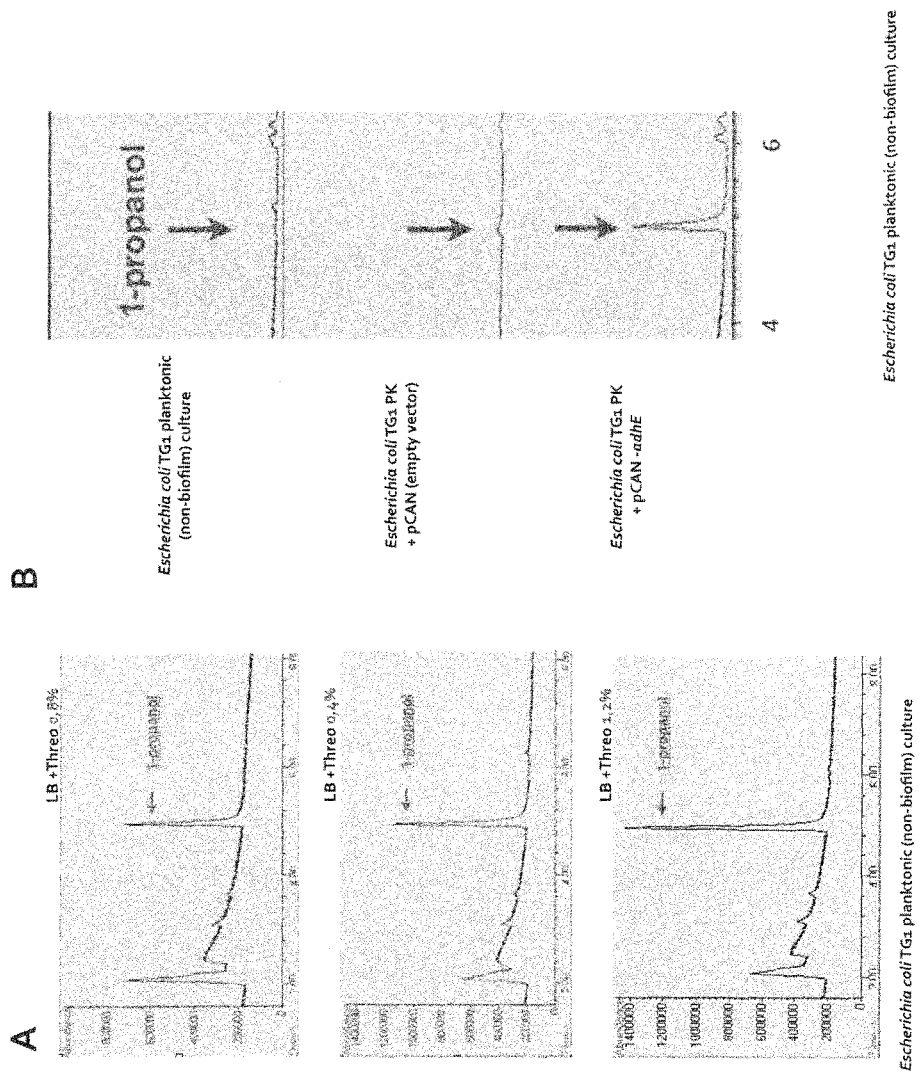
FIG. 9 shows *E. coli* production of 1-propanol in planktonic liquid culture and aerobic conditions. A. A dose dependent increase of propanol production is observed in the presence of increasing concentrations of threonine (0.4% (w/v), 0.8% (w/v) and 1.2% (w/v)). B. Overexpression of *E. coli* adhE gene from a plasmi enable 1-propanol production in liquid culture and aerobic conditions.

Example 5: Determination of E. coli Growth Conditions Leading to 1-Propanol Production in Liquid Planktonic Cultures Taking advantage of our results obtained on metabolic pathway leading to 1-propanol production in biofilms, we optimized growth conditions to obtain 1-propanol production in classic planktonic (liquid) cultures. We showed that although no propanol could be detected in *E. coli* liquid culture in overnight LB medium (test tube, 5 ml), addition of increasing concentration of threonine leads to a dose-dependent increase the production of 1-propanol (FIG. 9A). In parallel, we also showed that overexpression of *E. coli* adhE gene from a plasmid enable 1-propanol production in liquid culture (FIG. 9B).

These results indicate that 1-propanol production can be increased by addition of the amino acid threonine as a precursor of 1-propanol. In case of using a genetically engineered *E. coli* is not a regulatory issue, combining threonine addition and overexpression of adhE or other genes of the identified native metabolic pathway (tdcB- and ilvA, tdcE- and pflB; see FIG. 7) could further increase the yield of 1-propanol production, especially in mutants deleted for ptA, tdcD and ackA, in which the metabolic flow from threonine to 1-propanol could be increased. These strains and production strategy could be used with any biofilm forming *E. coli* (for instance TG1, MG1655 F) grown in continuous-flow microfermentors, continuously generating a large volume of culture supernatant containing 1-propanol. Alternatively, any *E. coli* background could be used to produced threonine-boosted 1-propanol production in classical liquid batch.

Example 6: Quantification of 1-Propanol Production from Biofilms and Planktonic Anaerobic Cultures Material

*E. coli* biofilms are cultured in continuous-flow microfermentors in Terrific Broth (TB) 1× or 2× medium or in Lysogeny Broth (LB) medium, with or without threonine 0.4%.

*E. coli* is grown in liquid condition (planktonic culture) and in anaerobic conditions in Terrific Broth 1× with or without threonine 0.4%.

Methods

Quantification of 1-propanol is performed by solid phase microextraction (SPME) firstly and by Gas chromatography Mass spectrometry (GC-MS) analysis of the *E. coli* biofilms in a second step. The method is calibrated with the reference compound 1-propanol-d7. GC uses a Shimadzu 2010 chromatograph with an extracting phase of cyanopropylphenylated PDMS and with an automatic Splitless/Split injection. The MS analysis uses a Shimadzu QP2010+ mass spectrometer, with ionization by electronic impact (70 eV) and detection by scanning.

Results

When biofilm is grown in continuous-flow fermentor during 24 h, stopped and analyzed immediately by SPME and GC-MS, 1-propanol quantification results are: 50 mg/l in LB, 300 mg/l in LB+threonine 0.4%, 150 mg/l in TB 1×, 350 mg/l in TB 1×+threonine 0.4%.

When biofilm is grown in continuous-flow fermentor during 24 h, stopped and let accumulated during 15 h, then analyzed by SPME and GC-MS, 1-propanol quantification results are: 255 mg/l in TB 1×, 1220 mg/l in TB 1×+threonine 0.4%.

When biofilm is grown in continuous-flow fermentor during 24 h, stopped and let accumulated during 24 h, then analyzed by SPME and GC-MS, 1-propanol quantification results are: 2500 mg/l in TB 1×+threonine 0.4%.

When biofilm is grown in continuous-flow fermentor during 24 h, stopped and let accumulated during 48 h, then analyzed by SPME and GC-MS, 1-propanol quantification results are:

228 mg/l (experiment 1), 236 mg/ml (experiment 2) in TB 1×

1405 mg/l (experiment 1), 1105 mg/l (experiment 2) in TB 2×

4875 mg/l (experiment 1), 3870 mg/l (experiment 2) in TB 1×+threonine 0.4%

3940 mg/l (experiment 1), 3790 mg/l (experiment 2) in TB 2×+threonine 0.4%.

When biofilm is grown in continuous-flow fermentor during 24 h, stopped and let accumulated during 96 h, then analyzed by SPME and GC-MS, 1-propanol quantification results are:

250 mg/l in TB 1×

3850 mg/l in TB 1×+threonine 0.4%

To conclude from the different conditions of biofilm culture, the richer is the culture medium, the more 1-propanol is produced, even without threonine. When threonine is added in culture medium, the richness of the medium has no more impact.

When bacteria are cultivated in planktonic anaerobic conditions during 24 h, stopped, and analyzed immediately by SPME and GC-MS, 1-propanol quantification results are:

375 mg/l (experiment 1) and 385 mg/l (experiment 2) in TB 1×

3245 mg/l (experiment 1) and 2960 mg/l (experiment 2) in TB 1×+threonine 0.4%

These results show that 1-propanol could be substantially produced in planktonic anaerobic conditions.

Example 7: 1-Propanol Production in Other Gram-Negative Anaerobic Bacteria (*Enterobacteria*)

Material and Methods

Inoculation and culture of the bacteria *Salmonella enterica, Shigella flexneri, Citrobacter rodentium* for 24 h at 37° C. in LB medium in anaerobic conditions (agitated flasks in anaerobic station). Propanol is detected by SPME-GCMS as described above.

Results

Figure 10:
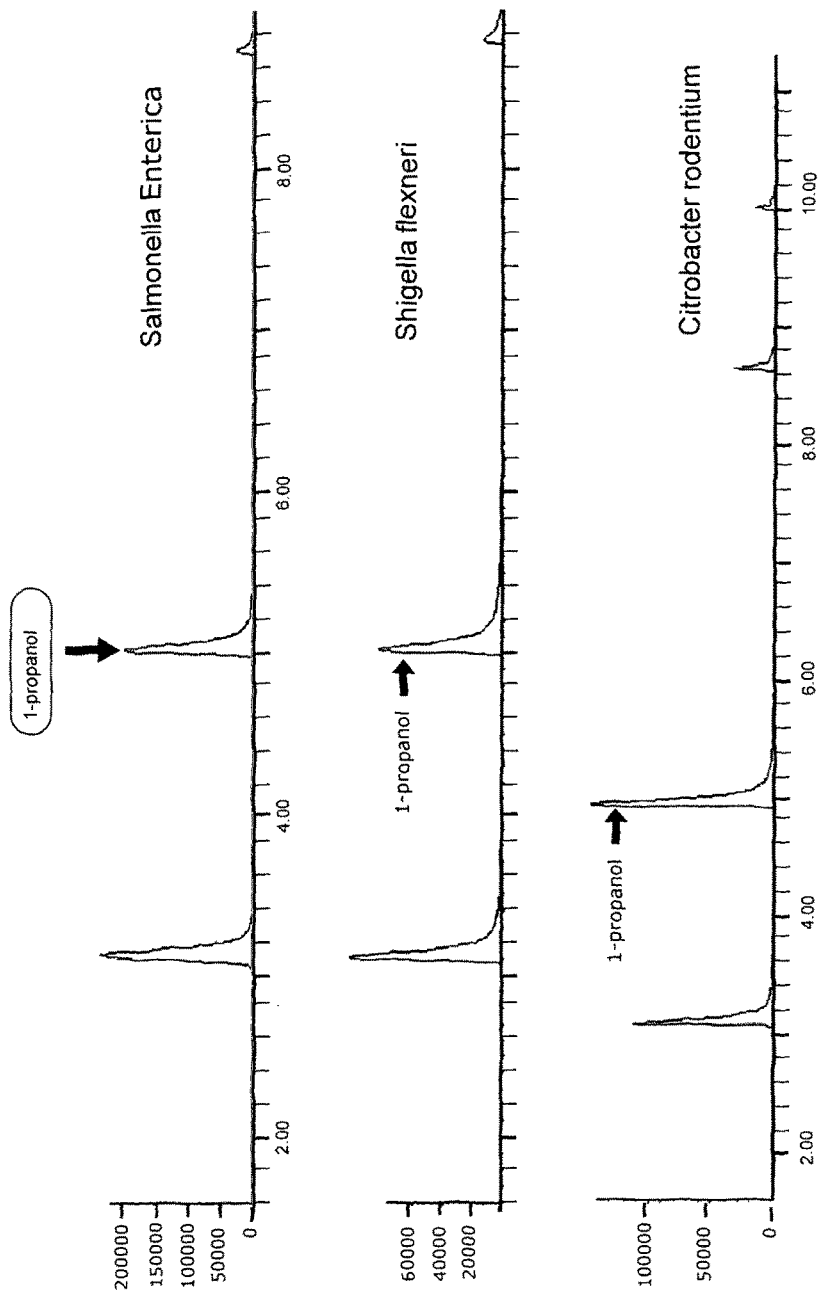
FIG. 10 shows SPME-GCMS-based detection of 1-propanol in bacterial cultures corresponding to the Gram-negative bacteria *Salmonella enterica, Shigella flexneri* and *Citrobacter rodentium*.

These results show that 1-propanol could be substantially produced in other Gram-Negative anaerobic bacteria (enterobacteria) such as *Salmonella enterica, Shigella flexneri*, and *Citrobacter rodentium* (FIG. 10).

Example 8: 1-Propanol is Produced from the Metabolic Degradation of Threonine

Figure 11:
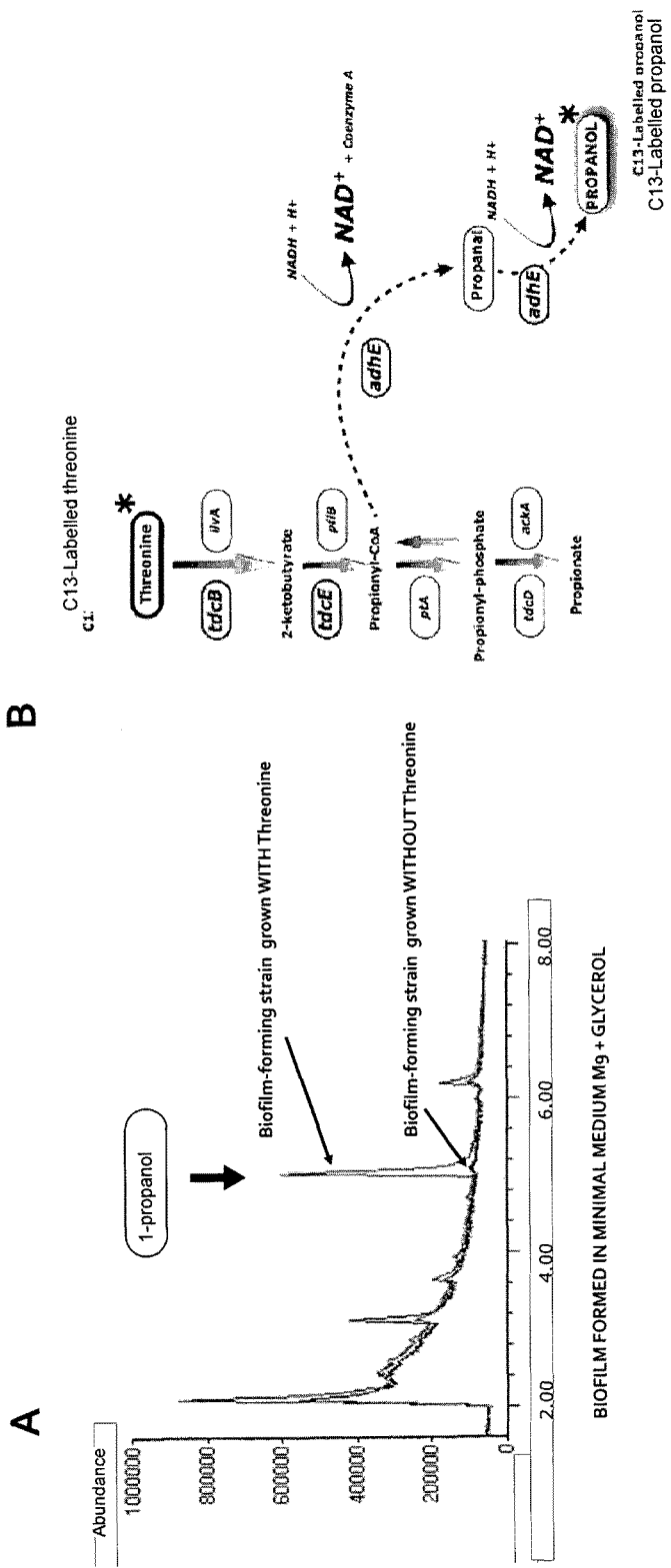
FIG. 11 shows that threonine is the biogenic precursor for 1-propanol production in *E. coli* biofilm (A) and illustrates the use of C13 isotopic labelled threonine to demonstrate that 1-propanol is produced from the metabolic degradation of threonine (B).
Figure 12:
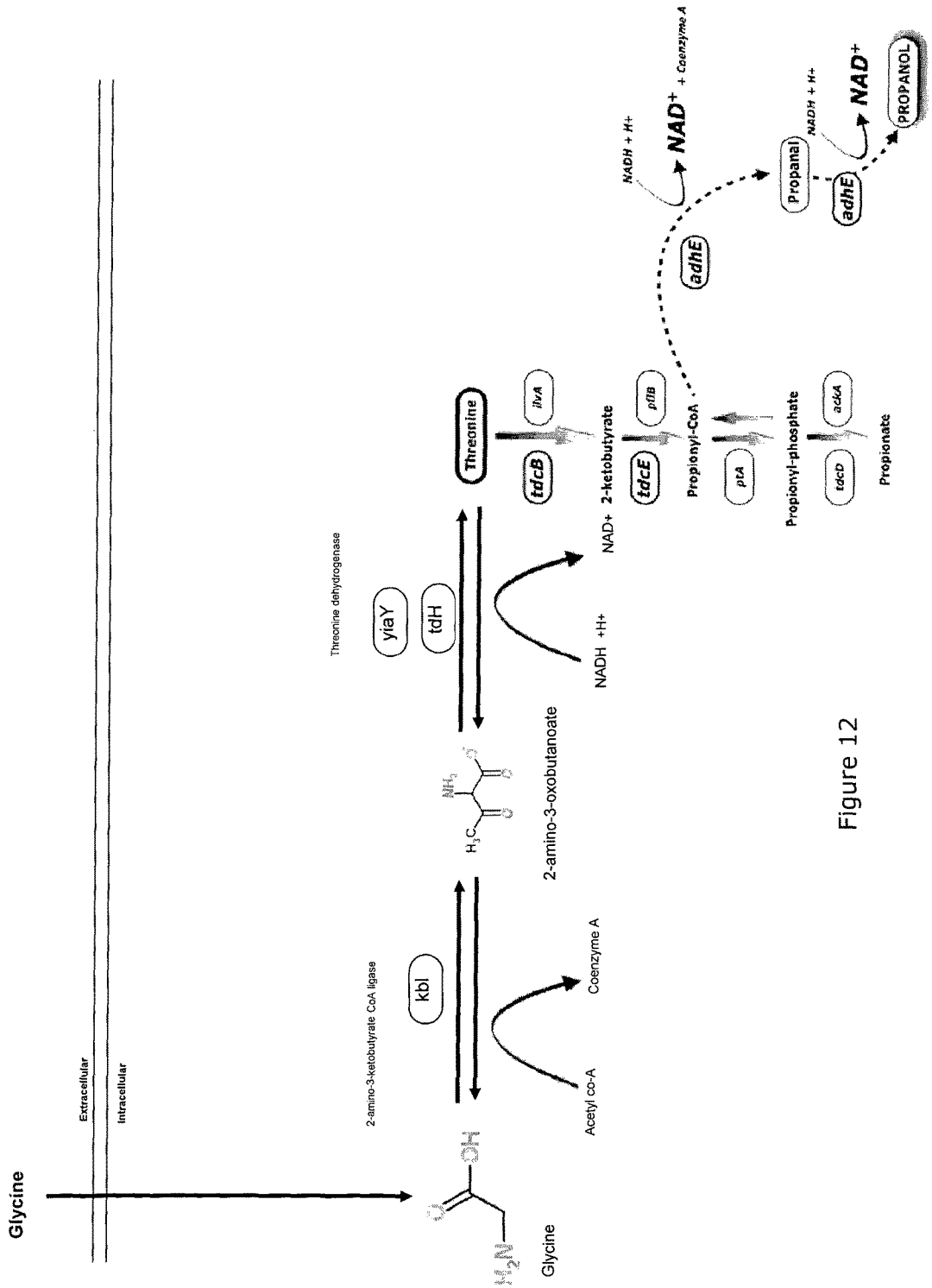
FIG. 12 shows 1-propanol production by stimulation of endogenous threonine biosynthesis, for example by addition of Glycine.

C13 isotopic labelled threonine was used to demonstrate that 1-propanol is produced from the metabolic degradation of threonine (FIG. 11B).

To determine that exogeneous threonine was preferentially used for propanol production, biofilm was produced by *Escherichia coli* TG1 in the minimum medium: M9 glycerol 0.4% (which does not contain threonine) for 48 h in continuous flow microfermentor. Then the flow with or without+Threonine 0.2% (corresponding to 50% of non labelled threonine and 50% of C13 labelled threonine (EURISO-TOP). After 48 h biofilm culture was interrupted for 15 h; and biofilm biomass was collected and analyzed by RMN to detect C13-labelled threonine metabolic degradation product. While no propanol could be detected in biofilm grown in M9 glycerol 0.4%, labelled propanol could be detected in biofilm grown in M9 glycerol 0.4% with C13 labelled Threonine 0.2% (corresponding to 50% of non labelled threonine and 50% of C13 labelled threonine (EURISO-TOP; FIGS. 11A and 11B).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

Atsumi, S. & J. C. Liao, (2008) Metabolic engineering for advanced biofuels production from *Escherichia coli. Curr Opin Biotechnol* 19: 414-419.

Choi, Y. J., J. H. Park, T. Y. Kim & S. Y. Lee, (2012) Metabolic engineering of *Escherichia coli* for the production of 1-propanol. *Metab Eng* 14: 477-486.

Deng, Y. & S. S. Fong, (2011) Metabolic engineering of *Thermobifida fusca* for direct aerobic bioconversion of untreated lignocellulosic biomass to 1-propanol. *Metab Eng* 13: 570-577.

Howell, D. M., H. Xu & R. H. White, (1999) (R)-citramalate synthase in methanogenic archaea. *J Bacteriol* 181: 331-333.

Jain, R. & Y. Yan, (2011) Dehydratase mediated 1-propanol production in metabolically engineered *Escherichia coli*. *Microb Cell Fact* 10: 97.

Rendueles, O., C. Beloin, P. Latour-Lambert & J. M. Ghigo, (2014) A new biofilm-associated colicin with increased efficiency against biofilm bacteria. *Isme J*.

Shen, C. R. & J. C. Liao, (2008) Metabolic engineering of *Escherichia coli* for 1-butanol and 1-propanol production via the keto-acid pathways. *Metab Eng* 10: 312-320.

Shen, C. R. & J. C. Liao, (2013) Synergy as design principle for metabolic engineering of 1-propanol production in *Escherichia coli. Metab Eng* 17: 12-22.

Srirangan, K., L. Akawi, X. Liu, A. Westbrook, E. J. Blondeel, M. G. Aucoin, M. Moo-Young & C. P. Chou, (2013) Manipulating the sleeping beauty mutase operon for the production of 1-propanol in engineered *Escherichia coli. Biotechnol Biofuels* 6: 139.

Yan, Y. & J. C. Liao, (2009) Engineering metabolic systems for production of advanced fuels. *J Ind Microbiol Biotechnol* 36: 471-479.

Eden, A., Van Nedervelde, L., Drukker, M., Benvenisty, N., Debourg, A., (2001) Involvement of branched-chain amino acid aminotransferases in the production of fusel alcohols during fermentation in yeast. *Appl. Microbiol. Biotechnol.* 55, 296-300.

Janssen, P. H., (2004) Propanol as an end product of threonine fermentation. *Arch. Microbiol.* 182, 482-486.

Ghigo, J M. (2003) Are there biofilm-specific physiological pathways beyond a reasonable doubt? *Res. Microbiol.* January-February; 154(1):1-8. Review.

Beloin C, Valle J, Latour-Lambert P, Faure P, Kzreminski M, Balestrino D, Haagensen J A, Molin S, Prensier G, Arbeille B, Ghigo J M. (2004) Global impact of mature biofilm lifestyle on *Escherichia coli* K-12 gene expression. *Mol. Microbiol.* February; 51(3):659-74.

Valle J, Da Re S, Schmid S, Skurnik D, D'Ari R, Ghigo J M. (2008) The amino acid valine is secreted in continuous flow bacterial biofilms. *J Bacteriol.* January; 190(1):264-74. Epub 2007 Nov. 2.

Rendueles O, Travier L, Latour-Lambert P, Fontaine T, Magnus J, Denamur E, Ghigo J M. (2011) Screening of *Escherichia coli* species biodiversity reveals new biofilm-associated anti-adhesion polysaccharides. MBio. May 10; 2(3):e00043-11.

Rendueles O, Kaplan J B, Ghigo J M. (2013) Antibiofilm polysaccharides. *Environ. Microbiol. February;* 15(2): 334-46. Epub 2012 Jun. 26. Review.

Rendueles O, Beloin C, Latour-Lambert P, Ghigo J M. (2014) A new biofilm-associated colicin with increased efficiency against biofilm bacteria. *ISME J.* June; 8(6): 1275-88.

Ghigo J M. (2001). Natural conjugative plasmids induce bacterial biofilm development. *Nature,* 412:442-445.

Baldoma L, Badia J, Obradors N, Aguilar J. (1988) Aerobic excretion of 1,2-propanediol by *Salmonella typhimurium*. *J Bacteriol.* June; 170(6):2884-5.

Sezonov et al., (2007). *Escherichia coli* Physiology in Luria-Bertani Broth. *Journal of Bacteriology,* 189(23), 8746-8749.

The invention claimed is:
1. A method of making 1-propanol, comprising the steps of:
 a) providing bacteria comprising tdcA-G genes and an adhE gene:
 b) culturing said bacteria under conditions suitable for expression of said tdcA-G genes and said adhE gene, thereby producing 1-propanol; and
 c) collecting said 1-propanol produced by the culture.
2. The method according to claim 1, wherein step a) comprises providing a cultured bacterial biofilm.

3. The method according to claim 2, wherein said cultured bacterial biofilm comprises bacteria seeded onto an artificial or natural solid substrate under conditions sufficient for the bacteria to form a biofilm.

4. The method of claim 1, wherein step a) comprises providing a planktonic bacterial culture.

5. The method according to claim 1, wherein said bacteria are cultured under anaerobic or microanaerobic conditions.

6. The method according to claim 1, wherein said bacteria are cultured in culture medium comprising threonine or glycine.

7. The method according to claim 6, wherein said culture medium is selected from Lvsogenv Broth (LB), Tryptic Soy Broth (TSB), Two x Yeast extract Tryptone (TYT), and Terrific Broth (TB).

8. The method according to claim 6, wherein said culture medium comprises at least 0.4% w/v threonine.

9. The method according to claim 6, wherein said culture medium comprises at least 0.1% w/v glycine.

10. The method according to claim 1, wherein said bacteria are enterobacteria.

11. The method according to claim 10, wherein said enterobacteria are *E. coli*.

12. The method according to claim 1, wherein said bacteria are genetically engineered to overexpress at least one gene selected from adhE, tdcB, ilvA, tdcE, and pflB.

13. The method according to claim 12, wherein said bacteria are genetically engineered to overexpress at least adhE and/or tdcB.

14. The method according to claim 1, wherein said bacteria are genetically engineered to reduce expression of at least one gene selected from ptA, tdcD, and ackA.

15. The method according to claim 14, wherein said bacteria are genetically engineered to reduce expression of at least tdcD.

16. The method according to claim 1, wherein said bacteria are cultured in planktonic culture under aerobic conditions.

17. The method according to claim 1, wherein the bacteria are cultured during at least 24 hours.

18. A genetically engineered bacteria which is genetically modified to overexpress at least the adhE and tdcB genes.

19. The bacteria according to claim 18, which is genetically modified to overexpress at least one of the ilvA, tdcE, and pflB genes.

20. The bacteria according to claim 18, which is genetically modified to reduce expression of at least one gene selected from ptA, tdcD, and ackA.

21. A bacterial culture comprising:
a) the genetically modified bacteria according to claim 18; and
b) a culture medium comprising threonine and glycine;
wherein said bacterial culture produces 1-propanol in liquid and/or gas form.

22. A method of making 1-propanol, comprising the steps of:
a) providing a wild-type enterobacteria biofilm,
b) culturing said enterobacteria biofilm in a culture medium comprising threonine or glycine; and
c) collecting said 1-propanol produced by the cultured enterobacteria biofilm.

23. The method according to claim 22, wherein the enterobacterial biofilm is grown on an artificial or natural solid substrate.

24. The bacterial culture according to claim 23, wherein the cultured enterobacterial biofilm is a cultured *E coli* biofilm.

25. The method according to claim 22, wherein said culture medium is selected from Lvsogenv Broth (LB), Tryptic Soy Broth (TSB), Two x Yeast extract Tryptone (TYT) and Terrific Broth (TB).

26. The method according to claim 22, wherein said culture medium comprises at least 0.4% w/v threonine.

27. The method according to claim 22, wherein said culture medium comprises at least 0.1% w/v glycine.

* * * * *